(12) United States Patent
Brahmbhatt

(10) Patent No.: US 7,704,732 B2
(45) Date of Patent: Apr. 27, 2010

(54) FERMENTATION UNIT WITH LIQUID NITROGEN COOLING

(75) Inventor: Sudhir R. Brahmbhatt, Glencoe, MO (US)

(73) Assignee: American Air Liquide, Inc., Fremont, CA (US)

( * ) Notice: Subject to any disclaimer, the term of this patent is extended or adjusted under 35 U.S.C. 154(b) by 936 days.

(21) Appl. No.: 11/277,993

(22) Filed: Mar. 30, 2006

(65) Prior Publication Data
US 2006/0281171 A1     Dec. 14, 2006

Related U.S. Application Data

(60) Provisional application No. 60/690,532, filed on Jun. 14, 2005.

(51) Int. Cl.
*C12M 1/02* (2006.01)
*C12N 1/00* (2006.01)

(52) U.S. Cl. .............. 435/289.1; 435/242; 435/303.1; 435/809

(58) Field of Classification Search .......... 435/303.1, 435/809, 289.1, 243
See application file for complete search history.

(56) References Cited

U.S. PATENT DOCUMENTS 3,445,342 A    5/1969  Freedman

| 4,164,127 | A | * | 8/1979 | Baumgartner | .................. 62/98 |
| 4,291,757 | A | * | 9/1981 | Redden | ................ 165/104.31 |
| 5,847,246 | A | * | 12/1998 | Hsu et al. | ...................... 585/1 |

FOREIGN PATENT DOCUMENTS

| EP | 0041702 A2 | * | 12/1981 |
| JP | 61195682 |   | 8/1986 |
| JP | 61289879 |   | 12/1986 |

OTHER PUBLICATIONS

International Search Report, Sep. 15, 2006.
Air Liquide Advanced Technologies, Brochure: "Alaska Cooling Units: control of your temperatures."

* cited by examiner

*Primary Examiner*—William H Beisner
(74) *Attorney, Agent, or Firm*—Christopher J. Cronin

(57) ABSTRACT

An integrated industrial plant includes various systems, all of which use a cryogenic liquid obtained from a common source. One system includes a fermentation unit, in which cold air, chilled by heat exchange with the cryogenic liquid, absorbs excess heat generated by the fermentation. Another system is a lyophilization unit, in which a refrigeration step is performed through the use of air that has been chilled by heat exchange with the cryogenic liquid. Another system is a device for freezing discrete samples of biological products, the samples being frozen by partial immersion in the cryogenic liquid. The invention substantially reduces the use of electric power, and provides systems which operate economically and reliably.

15 Claims, 4 Drawing Sheets

FIG.3 USE OF LIN IN LYOPHILIZATION PROCESS

FERMENTATION UNIT WITH LIQUID NITROGEN COOLING

CROSS-REFERENCE TO PRIOR APPLICATION

Priority is claimed from U.S. provisional patent application Ser. No. 60/690,532, filed Jun. 14, 2005, the disclosure of which is incorporated by reference herein.

BACKGROUND OF THE INVENTION

This invention relates to the use of industrial gases, such as nitrogen, in the operation of a multi-faceted industrial plant. The invention is especially useful in, but is not necessarily limited to, the manufacture of products for use in the fields of biotechnology, medicine, or health care.

A typical manufacturer of products in the biotechnology field may need to conduct a variety of processes in the same facility. Such processes may include deoxygenation, freezing, aerobic fermentation, palletizing, freeze drying, and inerting and blanketing. It may also be necessary to provide instrument air, i.e. a gas which can be safely and reliably used for operating instruments, such as pneumatic valves, in various processes. Such a plant may also require the ability to pulverize drug products, and to mix a highly viscous product into one of low viscosity.

In the prior art, some of the above functions may be performed with industrial gases, typically provided in compressed gas cylinders. Other functions, such as freezing and freeze drying, may be performed with compressors and conventional mechanical freezing techniques. Some of these components require electric power to operate. One object of the present invention is to reduce the amount of electric power required, and to operate a variety of components in a plant with a cryogenic liquid taken from a single source.

The following is a more detailed summary of various functions which may be performed in a facility for making products relating to the biotechnology and/or pharmaceutical industries. The following descriptions allude to the advantages that may be enjoyed by substituting industrial gases or cryogenic liquids for the mechanical or electrical means of performing the respective tasks.

1) Deoxygenation

Oxygen is removed from a solution by the introduction of nitrogen or argon. Typically, the nitrogen or argon is supplied in a lancing technique, using gas provided in cylinders. The choice of gas depends on the density and viscosity of the solution being treated. The selection of gas affects the time required for deoxygenation, and also affects the final oxygen concentration in the product. Gas supplied from cylinders is more expensive than gas provided in bulk form, so care must be taken in monitoring the quantity of gas used.

2) Freezing and Freeze-Drying

It is often necessary to freeze products, or to perform the process of freeze drying (lyophilization). Such steps are typically performed by conventional refrigeration systems, which require electricity, and which have moving parts requiring substantial maintenance. Conventional freezing has the disadvantage that an electrical power failure can shut the freezer down. Also, there is a practical limit to how much cooling can be done to a given quantity of cooling air, using conventional methods.

3) Aerobic Fermentation

The process of aerobic fermentation is probably the most widely used process in the biotechnology and pharmaceutical industries. Fermentation relies on microorganisms to produce a desired product, as a cost effective alternative to a more expensive synthetic manufacturing method. Most prior art aerobic fermenters use air compressors to supply air to the fermenters, so as to meet the oxygen required by the microorganisms in the fermentation process. In the event of an electrical power failure, the fermentation unit will need to be shut down, and may cause the operator to lose expensive batches of fermentation medium.

4) Palletizing

In a manufacturing process in the biotechnology field, mechanical or other methods are used to palletize drugs or other products.

5) Product Freezing

In the biotechnology field, it is known to freeze a diagnostic product, or a pharmaceutical product, provided in vials arranged on a tray. The tray of vials is carried to a mechanical freezer and secured in the freezer prior to closing a door. This activity can become a safety issue, as workers must carry heavy loads into and out of the freezer, causing possible back injuries. Also, the frequent opening and closing of the freezer door causes a significant delay in the freezing process. A failure of electrical power also causes a significant interruption to this process.

6) Inerting and Blanketing

A typical arrangement for inerting uses a bank of cylinders connected to a manifold, for supplying gases such as nitrogen and argon. Since the gas comes into contact with the finished product, the quality of the inerting medium is critical. A failure of electrical power can shut down the air compressors, causing instrumentation to cease operation, and causing failure of the entire inerting and blanketing process.

7) Instrument Air for Process Control

It is common, in the prior art, to use air compressors to provide instrumentation air to power various components, such as pneumatically operated valves. A failure of electrical power can easily cause a major interruption in the operation of the process.

8) Pulverizing of Drug Products

In many cases, it is necessary to pulverize a pharmaceutical product. Conventional mechanical pulverizing methods may change the quality of the finished product. In particular, the heat generated by mechanical pulverization may increase the temperature of the product, causing the loss of low-boiling hydrocarbons, and undesirably changing the quality of the product. Such problems are not encountered with cryogenic grinding. Similar considerations apply where it is desired to mix a highly viscous product into a product of lower viscosity, such as in mixing fat with protein.

The present invention provides an integrated system and method, wherein it is possible to use an industrial gas, such as nitrogen, coming from a single source, to operate a plurality of units in a facility. The invention also includes several novel subsystems suitable for use in an integrated facility which manufactures biotechnological or pharmaceutical products.

SUMMARY OF THE INVENTION

The present invention includes an integrated plant having a plurality of distinct systems, all of which rely, in whole or in part, on cryogenic liquid, or vaporized cryogenic liquid, obtained from a single source. A single source of cryogenic liquid, preferably nitrogen, is used to operate a cryogrinding unit, a cryocooling unit, a cryogen rapid cooling unit, and a diagnostic products manufacturing unit. The cryogenic liquid is vaporized to form a gas, and this gas is used for inerting and blanketing, for lyophilization, for fermentation, and for supplying instrument air. All of the above units and processes may be operated simultaneously. The invention reduces the need for electric power, insofar as certain functions, such as refrigeration, are performed by heat exchange with the cryogenic liquid, instead of through the use of compressors and the like.

The invention also includes a fermentation system which forms one of the units in the integrated system described above. The fermentation system includes a fermentation vessel, a source of cold water, and a source of cryogenic liquid. The cold water is further chilled by heat exchange with the cryogenic liquid. The chilled water is then introduced into the vessel, so as to absorb the heat generated by the fermentation process. The above arrangement makes it feasible to increase the productivity of the fermentation process, by adding oxygen to the vessel, since the additional heat generated by fermentation can be conveniently carried away by the chilled water. The source of cryogenic liquid is preferably the same as the source used to operate the other units in the integrated system described above.

The invention also includes a lyophilization system which makes advantageous use of the cryogenic liquid described above. The lyophilization system includes a chamber in which the products to be freeze-dried are placed on shelves which are heated or cooled. In the lyophilization process, the products are first frozen, and the surrounding air pressure is reduced, so that a subsequent application of a small amount of heat will cause ice, previously formed on the products, to sublimate into water vapor. The water vapor is conveyed to a refrigeration unit, where it condenses on a refrigeration coil, and can then be easily removed as liquid. In the present invention, the refrigeration coil contains cold air that has been chilled by heat exchange with the above-mentioned cryogenic liquid. Thus, the present invention reduces or eliminates the need for a mechanical refrigeration system in the lyophilization process.

Another aspect of the invention is a system and method for preparation of frozen biological products. A plurality of vials, each being partly filled with the product to be frozen, are conveyed on a movable belt. A cryogenic liquid, preferably from the same source described above, is ducted to the vicinity of the belt, and is poured around the vials, causing at least some of the vials to become partly immersed. A vaporized cryogenic liquid, such as gaseous nitrogen, is injected into the head spaces of each of the vials, and the vials are sealed. The vials can now be transported, with appropriate cooling means such as dry ice, to a point of use.

The invention therefore has a primary object of providing an integrated system for performing various industrial processes, all of which processes rely upon a single source of cryogenic liquid.

The invention has the further object of providing an integrated system for producing biological or medical products, using a single source of cryogenic liquid.

The invention has the further object of providing a fermentation unit which is cooled by a medium that has been chilled through heat exchange with a cryogenic liquid.

The invention has the further object of providing a lyophilization unit in which a refrigeration step is performed by using air that has been chilled through heat exchange with a cryogenic liquid.

The invention has the further object of providing a unit for freezing of a plurality of diagnostic products, using a cryogenic liquid.

The invention has the further object of reducing the cost of operating various biological processes, such as fermentation and lyophilization, through the use of a cryogenic liquid for purposes of cooling.

The invention has the further object of providing an industrial plant having a reduced dependence on electric power.

The invention has the further object of providing an industrial plant having systems of enhanced reliability.

The reader skilled in the art will recognize other objects and advantages of the invention, from a reading of the following brief description of the drawings, the detailed description of the invention, and the appended claims.

DETAILED DESCRIPTION OF THE INVENTION

Figure 1:
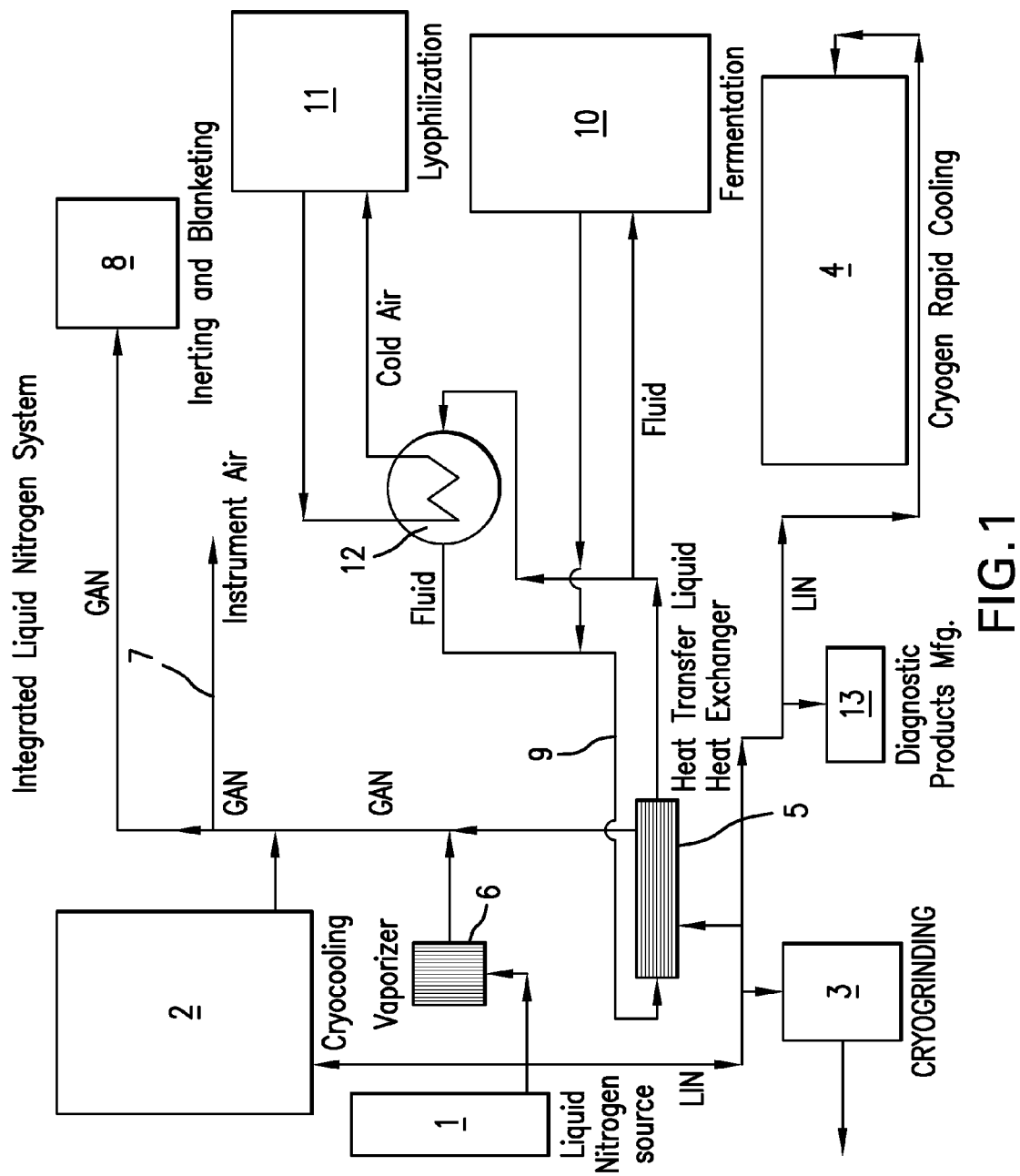
FIG. 1 provides a schematic diagram of an integrated system in which a single source of liquid nitrogen is used to operate a plurality of processes in the same facility.

FIG. 1 provides a schematic diagram of a facility for producing biological and/or pharmaceutical products, the facility including various subsystems which operate with a cryogenic liquid, such as nitrogen, from a single source.

The nitrogen used in the system of FIG. 1 is stored in cryogenic storage tank 1. Liquid nitrogen from tank 1 may be tapped directly, and used, in the liquid phase, in cryocooling unit 2, cryogrinding unit 3, and unit 4 for cryogen rapid cooling. The cryocooling unit 2 differs from the cryogen rapid cooling unit 4, in that unit 2 is used for cooling a process stream, while unit 4 operates a process for making pellets or other discrete products. The cryogrinding unit allows the user to grind a product to a very fine size without sacrificing quality. Liquid nitrogen is also conveyed directly to diagnostic products manufacturing unit 13, which is illustrated more fully in FIG. 4, and which is described in more detail later.

Some of the liquid nitrogen passes through heat exchanger 5, where it absorbs heat from a heat transfer liquid and then becomes gaseous nitrogen (GAN). The heat transfer liquid is preferably a material such as heptane or pentane, or another liquid having very good heat transfer capabilities under cryogenic conditions.

Some of the liquid nitrogen from tank 1 also passes into vaporizer 6, where it also becomes gaseous nitrogen (GAN). As shown in the figure, gaseous nitrogen may be conveyed, through line 7, for use as instrument air, i.e. for the operation of pneumatic valves and other instruments (not shown) requiring an inert or relatively inert gas. Gaseous nitrogen is also used to operate inerting and blanketing unit 8. Because the liquid nitrogen is converted to gaseous nitrogen by indirect contact with a heat exchange medium, the quality of the nitrogen is maintained, and it can be satisfactorily used for inerting and blanketing. The use of the gaseous nitrogen as instrument air extends the life of the instrument, due to the very low moisture content of the instrument air, and also reduces or eliminates the need for power to drive a compressor for supplying instrument air.

As noted above, the heat exchanger 5 provides a means for cooling a heat transfer liquid, by thermal contact with the liquid nitrogen. The heat transfer liquid flows in conduit 9. This heat transfer liquid is used for two purposes. First, it is directed into the fermentation unit, as will be explained in more detail later. Secondly, it flows through heat exchanger 12, which cools the air being circulated through lyophilization unit 11. The operation of the lyophilization unit will be described in more detail later.

Note that all of the units shown in FIG. 1 can be operated simultaneously, or in any subcombination. All of these units depend on nitrogen (or another inert, or nearly inert, material), preferably drawn from a single source.

Figure 2:
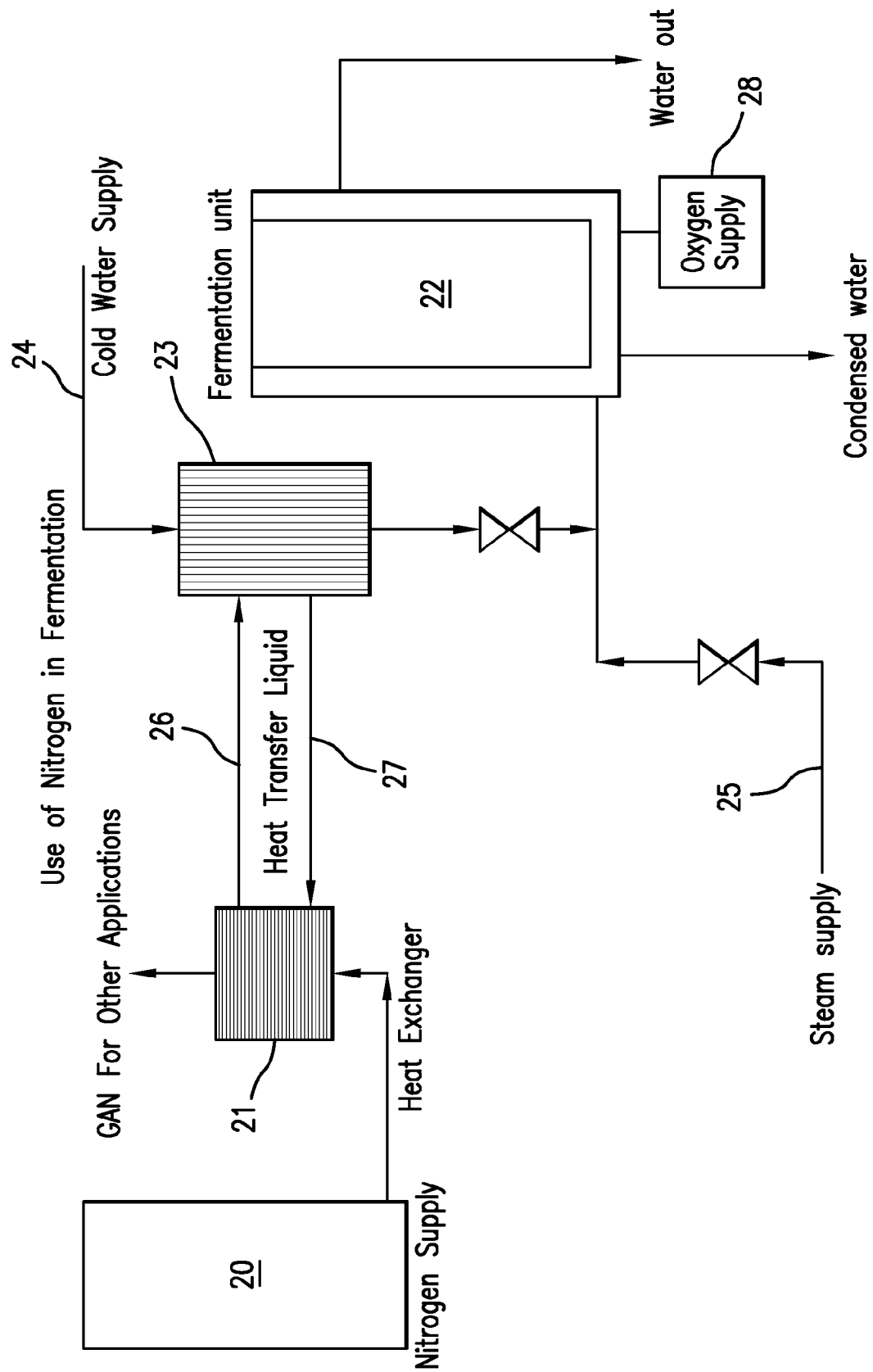
FIG. 2 provides a schematic diagram of a fermentation system constructed according to the present invention.

FIG. 2 provides a schematic diagram which contains further details about the fermentation unit symbolically illustrated in FIG. 1.

A fermentation unit requires a means of regulating the temperature in the fermentation vessel. The fermentation reactions generate heat. If the temperature in the vessel becomes too high, the microorganisms in the vessel will gradually lose productivity, and the fermentation process will eventually cease. On the other hand, if the temperature is too low, the microorganisms will not be active in promoting the desired reactions.

In FIG. 2, liquid nitrogen from supply 20 (which corresponds to source 1 of FIG. 1) passes through heat exchanger 21 (which corresponds to heat exchanger 5 of FIG. 1). The remaining components of FIG. 2 are included within unit 10 of FIG. 1. That is, a fermentation vessel 22 is connected to heat exchanger 23 which is connected to receive a supply of cold water, through line 24, and to a source of steam, which is conveyed through line 25. The incoming water is chilled by heat exchange with the heat transfer liquid flowing in lines 26 and 27.

The output of an aerobic fermentation unit can be increased by introducing substantially pure oxygen into the fermentation vessel, such as from oxygen supply 28. However, adding oxygen to the vessel will increase the heat generated, because of the increased activity of the microorganisms. The system will tolerate this increased activity if there is an effective means for carrying away the excess heat. The chilled water introduced into the vessel accomplishes this purpose of dissipating the excess heat, and prevents excessive buildup of heat in the vessel. As shown in FIG. 2, the water is indirectly chilled by the liquid nitrogen.

Figure 3:
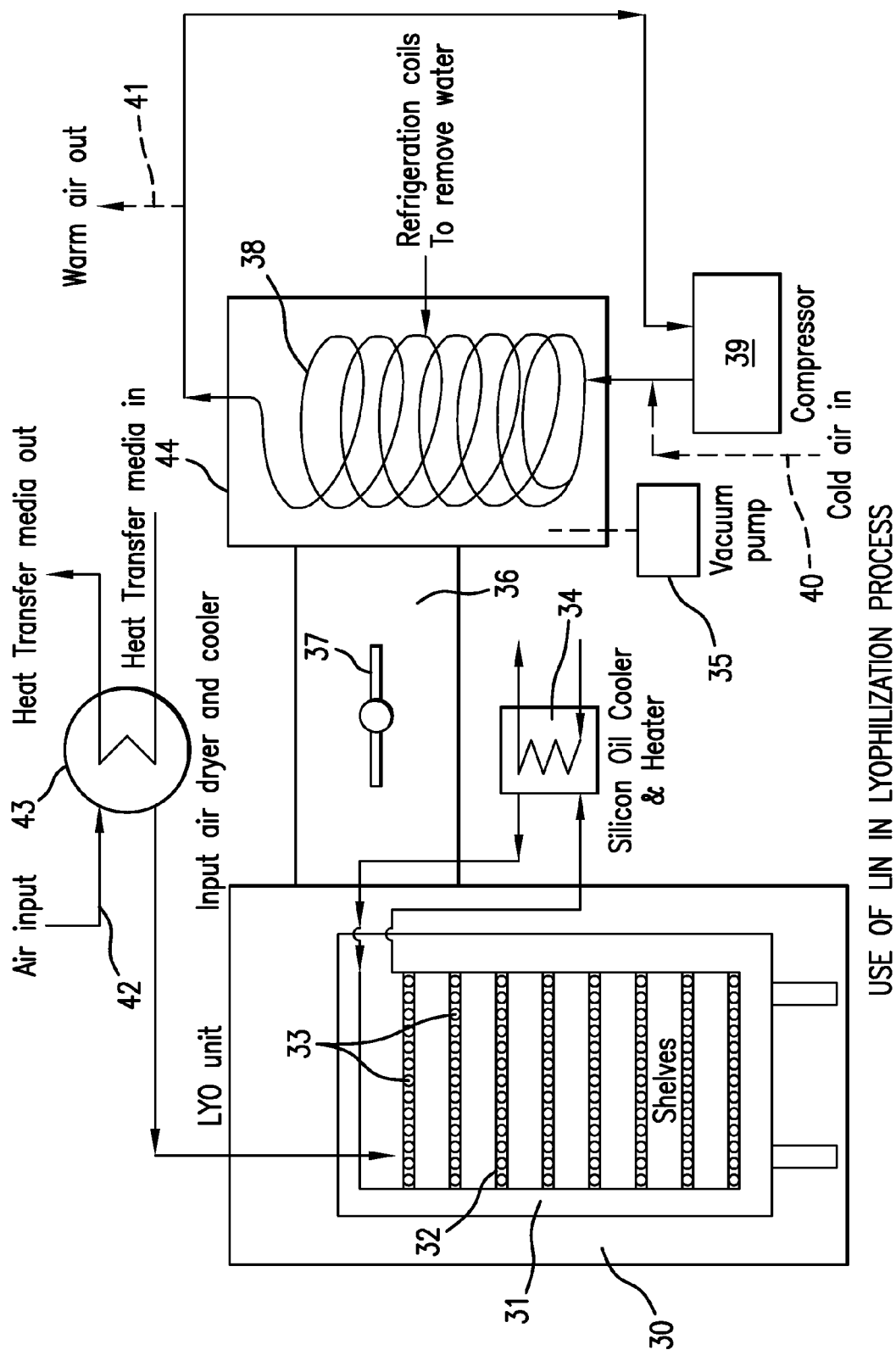
FIG. 3 provides a schematic diagram of a lyophilization system constructed according to the present invention.

FIG. 3 provides a schematic diagram of a lyophilization unit made according to the present invention. Lyophilization, also known as freeze drying, removes free water from a solution. The process is especially useful in the medical or biotechnology industry because it extends the shelf life of a solution, such as is used in a diagnostic test, and because it replaces a freezing process. In general, an enzyme-based material tends to become activated upon contact with moisture. Conversely, removing the moisture reduces the amount of enzyme activity.

As shown in FIG. 3, lyophilization unit 30 includes a cabinet 31 having a plurality of shelves 32. The product to be freeze dried is provided in open containers (not shown) placed on the shelves. Within the shelves are a plurality of tubes or channels 33, through which a heat transfer medium is circulated. In a preferred embodiment, the heat transfer medium is silicon oil, which is heated or cooled, by conventional means, in unit 34. The silicon oil heater and cooler is entirely conventional; for this reason, further details concerning the heat transfer medium used in this component are not shown.

The freeze drying process is initiated by cooling the product and by creating a partial vacuum. Ice forms on the product, due to the cooling step. When the pressure in the cabinet 31 is sufficiently low, the application of a small amount of heat, through the medium of the silicon oil, will cause the ice to sublimate into water vapor, which can then be easily removed from the vessel. The net effect is to cause liquid to be released from the product.

The partial vacuum is produced by vacuum pump 35. This pump draws air from lyophilization unit 30, through conduit 36, and into condensing unit 44. Valve 37 can be used to open or close the conduit 36. The condensing unit includes refrigeration coil 38 for absorbing heat from air drawn from the lyophilization unit.

The heat absorbing medium flowing in the refrigeration coil can be a conventional refrigerant, which is liquefied by compressor 39 in a conventional refrigeration system. Alternatively, and preferably, the refrigeration is provided by cold air conveyed through conduit 40. This cold air is the same as the cold air cooled in heat exchanger 12 of FIG. 1. The cold air becomes warmed, by heat exchange with the air pulled from the lyophilization unit, and exits the system through conduit 41. This is the same stream as the gas which exits unit 11, and returns to heat exchanger 12, in FIG. 1. The effect is to cause the water vapor, drawn from the cabinet 31, to condense into water, which can then be easily removed.

The lyophilization process also includes the introduction of dry air into the lyophilization unit. The drier the air, the more water it can hold, and the more water can be released from the product into the dry air. A stream of ambient air enters through conduit 42, and is cooled in heat exchanger 43. The heat transfer medium used to cool the air stream may be the same heat transfer liquid used in heat exchangers 5 and 12 of FIG. 1. When the incoming air is cooled, moisture is precipitated out of the air, and the air that proceeds to the lyophilization unit 30 is substantially dried. This dried air absorbs moisture given off by the products in the lyophilization unit, and vents from the lyophilization unit through conduit 36.

In the process represented in FIG. 3, the nitrogen-cooled cold air entering through conduit 40 is used either as a supplement to a conventional refrigerant that is compressed by compressor 39, or it can be used instead of such refrigerant. Use of the nitrogen-cooled cold air therefore eliminates or reduces the need for the compressor 39. Thus, an advantage of the use of the present invention is that one may shut down the compressor, thereby reducing the consumption of electrical power.

Figure 4:
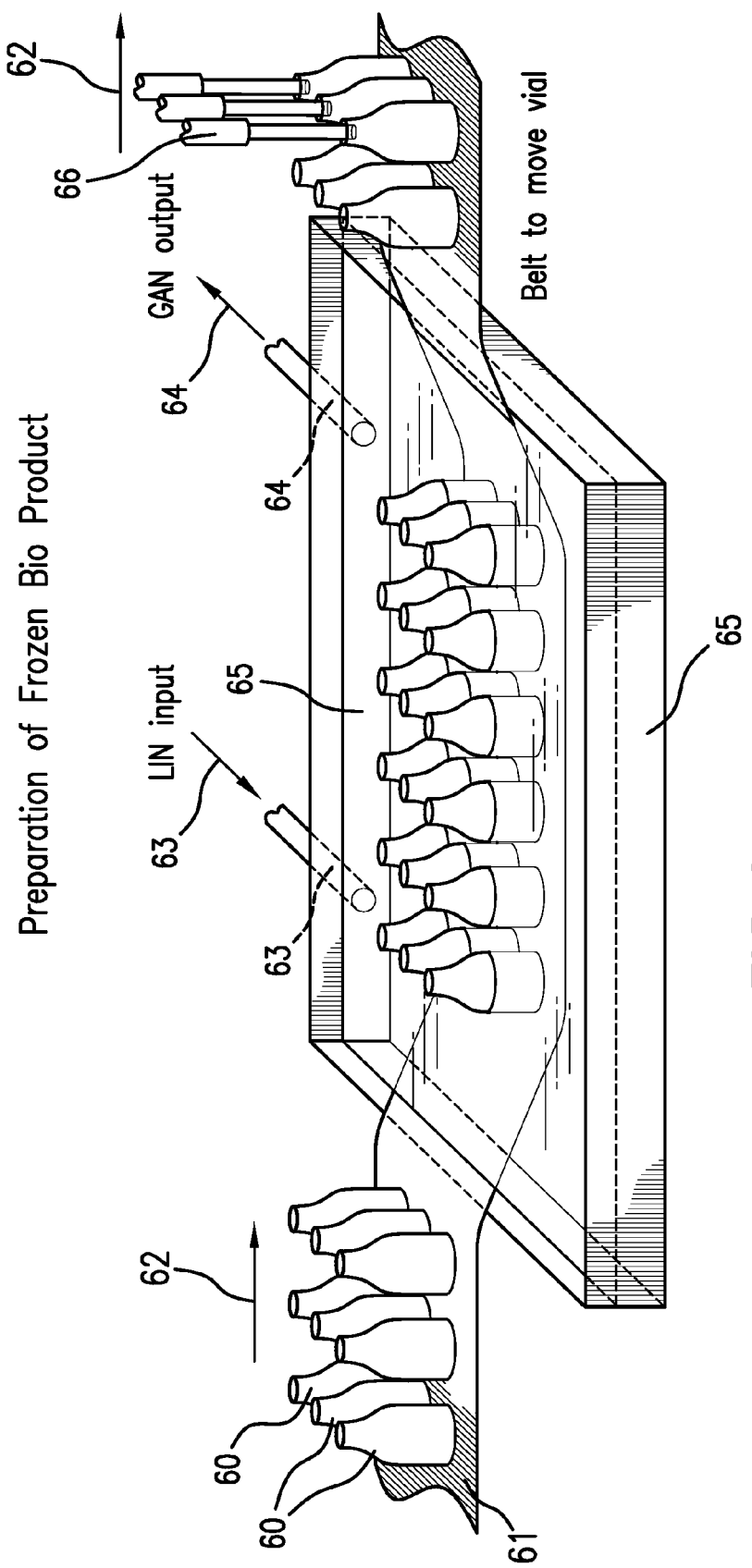
FIG. 4 provides a partially schematic and partially perspective diagram of a unit for preparation of frozen biological products, according to the present invention.

FIG. 4 provides a diagram of the process represented in block 13 of FIG. 1. This process comprises the preparation of frozen biological products. For example, the process could be used to make diagnostic products, such as blood serum to be mixed with a blood sample to perform a medical test. The process could be used to make other products having a biotechnological connection. In general, freezing of such products stops enzymatic activity, and preserves such products for a long time. To insure the desired preservation, the products must be frozen quickly, and are typically transported, to the place of use, in a special container with dry ice to keep the products frozen.

In the process represented in FIG. 4, the product samples are provided in a plurality of vials 60, typically made of glass, and arranged on belt 61 which is moved through the freezing unit as indicated by arrows 62. Liquid nitrogen is introduced through inlet conduit 63, into trough 65. This conduit is the same as the conduit leading to block 13 in FIG. 1. In practice, the trough has a cover (not shown), such that the trough and cover together define a tunnel, into which the vials are transported. The cover is not shown in FIG. 4, for purposes of clarity of illustration.

The liquid nitrogen is introduced in sufficient quantity, in the above-described freezing zone or tunnel, such that the vials are partially, but not completely, immersed in the liquid. As shown in FIG. 4, the belt 61 is sufficiently flexible that, upon passing over the boundary of the trough, it can move downward sufficiently that the vials become partially immersed in the liquid nitrogen. The liquid nitrogen therefore does not directly touch the product, but only surrounds the vials containing the product. The liquid nitrogen which has been vaporized leaves the unit as gaseous nitrogen, through outlet conduit 64.

After the vials have been processed in the trough, they exit the tunnel, as shown in FIG. 4, arriving at a station where gaseous nitrogen is introduced into the head space of each vial. Injection port 66 is used to introduce the gaseous nitrogen into the vial. In the preferred embodiment, there are a plurality of such injection ports operating simultaneously, as shown.

The effect of the liquid nitrogen is to freeze the product in the vials very quickly. After the gaseous nitrogen has filled the head space of the vials, the vials are sealed by attaching and closing their caps or lids. The vials are ready to be shipped, in a refrigerated condition, such as in dry ice, to the point of use. Note that, in the above process, liquid nitrogen never comes into direct contact with the biological product. Gaseous nitrogen, however, does contact such product.

The present invention therefore has the advantage of enabling the performance of many different tasks, using a single source of cryogenic liquid, such as liquid nitrogen. Since the nitrogen can be supplied in a system having no moving parts, and requiring no electric power, the system can reduce the amount of electric power required in operating an industrial plant. The use of the present invention improves the productivity and yield of a plurality of biological processes, at least in part because the nitrogen from a single source can be channeled into many uses. The invention therefore provides a means for reducing costs of production.

The invention has the further advantage that it can be implemented with only a nominal capital investment. The ducting implied in the drawings can easily be implemented by retrofitting an existing plant. The cost of capital is further reduced due to the use, for example, of one heat exchanger to service both fermentation and lyophilization units.

The present invention also has the advantages of improved reliability, and reduction in maintenance cost, because it relies on a system having few or no moving parts. The use of cryogenic liquids has the potential to improve the quality of the biological products, because such liquids are inherently able to cool a product to lower temperatures than would be convenient or possible with mechanical refrigeration systems.

The invention can be modified by the addition of further subsystems requiring liquid or gaseous nitrogen. Such modifications, which will be apparent to those skilled in the art, should be considered within the spirit and scope of the following claims.

What is claimed is:

1. A fermentation system, comprising:
   a) a source of cryogenic liquid,
   b) a first heat exchanger connected to said source of cryogenic liquid,
   c) a second heat exchanger connected to a source of water,
   d) heat transfer liquid circulation lines including a heat transfer liquid that extend between said first and second heat exchangers, wherein heat is transferred to said cryogenic liquid from said water to produce chilled water, and
   e) a fermentation vessel connected to receive chilled water from said second heat exchanger so as to dissipate heat generated in the vessel.

2. The fermentation system of claim 1, wherein the source of cryogenic liquid is connected to a plurality of distinct systems at a same location as the fermentation system.

3. The fermentation system of claim 2, wherein said plurality of distinct systems is selected from the group consisting of a cryocooling system, a cryogrinding system, a cryogen rapid cooling system, a diagnostic products manufacturing unit, an inerting and blanketing unit, and a lyophilization unit.

4. The fermentation system of claim 2, wherein the source of cryogenic liquid is connected to a vaporizer for providing cold gas to at least some of said plurality of systems.

5. The fermentation system of claim 2, wherein said systems are selected from the group consisting of a cryocooling system, a cryogrinding system, a cryogen rapid cooling system, a diagnostic products manufacturing unit, an inerting and blanketing unit, and a lyophilization unit.

6. A fermentation system comprising:
   a) a fermentation vessel,
   b) a source of water,
   c) a source of cryogenic liquid,
   d) a heat exchanger unit adapted to cool said water through heat exchange with said cryogenic liquid via a heat exchange fluid, and
   e) cool water introduction lines adapted to introduce said cooled water into said fermentation vessel so as to dissipate heat generated in the vessel.

7. The fermentation system of claim 6, wherein the heat exchanger unit includes at least one heat exchanger connected to the source of cryogenic liquid, the heat exchanger comprising means for producing a vaporized cryogenic liquid for use in at least one other application.

8. The fermentation system of claim 6, wherein the source of cryogenic liquid is connected to supply at least one other distinct system with cryogenic liquid, in parallel with the fermentation system.

9. The fermentation system of claim 8, wherein said at least one other distinct system is selected from the group consisting of a cryocooling system, a cryogrinding system, a cryogen rapid cooling system, a diagnostic products manufacturing unit, an inerting and blanketing unit, and a lyophilization unit.

10. The fermentation system of claim 6, further comprising a supply of oxygen connected to the fermentation vessel.

11. A method of operating a fermentation system, comprising:
   a) cooling a stream of water by heat exchange with a cryogenic liquid, wherein said step of cooling comprises circulating a heat transfer liquid between said cryogenic liquid and said stream of water; and
   b) introducing said cooled water into a fermentation vessel, wherein the cooled water dissipates heat generated in the vessel.

12. The method of claim 11, further comprising introducing additional oxygen into the vessel, and repeating steps (a) and (b) to an extent necessary to dissipate additional heat caused by the step of introducing additional oxygen, wherein the productivity of the fermentation system is increased.

13. The method of claim 11, further comprising using the cryogenic liquid in at least one distinct system simultaneously with its use in the fermentation system.

14. The method of claim 13, further comprising the step of selecting said at least one distinct system from the group consisting of a cryocooling system, a cryogrinding system, a cryogen rapid cooling system, a diagnostic products manufacturing unit, an inerting and blanketing unit, and a lyophilization unit.

15. The method of claim 11, further comprising selecting said cryogenic liquid to be nitrogen.

* * * * *